A United States Patent [19]
Untch et al.

[11] 4,177,280
[45] Dec. 4, 1979

[54] BICYCLO[3.1.0]HEXYL-SUBSTITUTED CARBONYLAMINOPHENOXY CARDIOVASCULAR AGENTS

[75] Inventors: Karl G. Untch; Belig Berkoz, both of Los Altos; Stefan H. Unger, Palo Alto, all of Calif.

[73] Assignee: Syntex (U.S.A.) Inc., Palo Alto, Calif.

[21] Appl. No.: 921,371

[22] Filed: Jul. 3, 1978

[51] Int. Cl.$^2$ .................. C07C 103/19; C07C 127/15; A61K 31/42; A61K 31/17

[52] U.S. Cl. ............................ 424/272; 260/553 A; 260/557 B; 260/465 D; 424/300; 424/322; 424/324; 424/304; 560/29; 548/215; 548/232

[58] Field of Search ........ 260/307 FA, 553 A, 557 B, 260/465 D; 424/272, 322, 324, 304

[56] References Cited

U.S. PATENT DOCUMENTS

| | | | |
|---|---|---|---|
| 4,034,009 | 7/1977 | Zolss et al. | 260/553 A |
| 4,035,420 | 7/1977 | Berntsson et al. | 260/553 A |
| 4,038,313 | 7/1977 | Wilhelm | 260/553 A |
| 4,038,414 | 7/1977 | Jaeggi et al. | 260/553 A X |
| 4,063,025 | 12/1977 | Murakami et al. | 260/553 A X |

*Primary Examiner*—Thomas A. Waltz
*Attorney, Agent, or Firm*—Richard J. Hammond; Gerard A. Blaufarb

[57] ABSTRACT

1-Alkylamino-3-(4-[(endobicyclo[3.1.0]hex-6-yl)alkylureido]-1-phenoxy)-2-propanol and substituted derivatives thereof; 1-alkylamino-3-(4-[(endobicyclo[3.1.0-]hex-6-yl)-alkylcarbonylamino]-1-phenoxy)-2-propanol and substituted derivatives thereof; and 1-alkylamino-3-(4-[(endobicyclo-[3.1.0]hex-6-yl)alkoxycarbonylamino]-1-phenoxy)-2-propanol and substituted derivatives thereof as well as methods for preparing such compounds are disclosed. 5-(4-[(Endobicyclo[3.1.0]hex-6-yl)alkylureido]-1-phenoxy) methyl-3-alkyl-2-optionally substituted oxazolidine and derivatives thereof; 5-(4-[(endobicyclo[3.1.0]hex-6-yl alkylcarbonylamino]-1-phenoxy)methyl-3-alkyl-2-optionally substituted oxazolidine and derivatives thereof; and 5-(4-[(endobicyclo[3.1.0]hex-6-yl)alkoxycarbonylamino]-1-phenoxy)-methyl-3-alkyl-2-optionally substituted oxazolidine and derivatives thereof and methods for preparing these compounds are also disclosed. These compounds exhibit cardiovascular activity and are useful in the treatment of abnormal heart conditions as well as hypertension in mammals. The bicyclo-2-propanols are prepared by treatment of the corresponding 1,2-epoxy-3-(4-[(endobicyclo[3.1.0]hex-6-yl)alkylureido, alkylcarbonylamino or alkoxycarbonylamino-1-phenoxypropane, with the desired alkylamine or by base or acid hydrolysis of the corresponding 5-(4-[(endobicyclo[3.1.0]-hex-6-yl)alkylureido, alkylcarbonylamino or alkoxycarbonylamino]-1-phenoxy)-methyloxazolidine. The lattercompounds are prepared from the corresponding 1-alkylamino-3-(4-[(endobicyclo[3.1.0]-hex-6-yl)alkylureido, alkylcarbonylamino or alkoxycarbonylamino]-1-phenoxy)-2-propanol by treatment with an aldehyde having the desired optional substituent.

61 Claims, 4 Drawing Figures

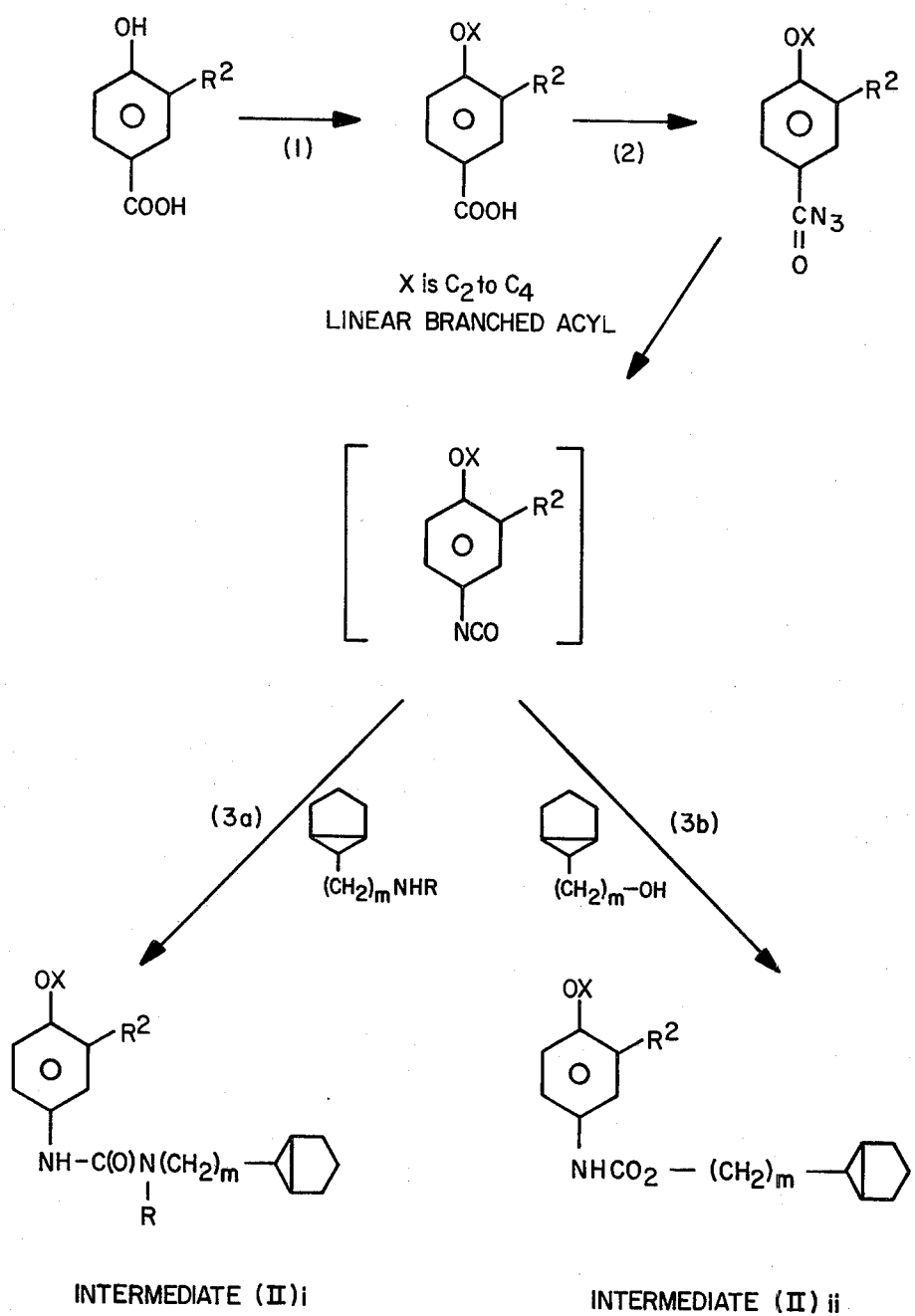
FIG_1

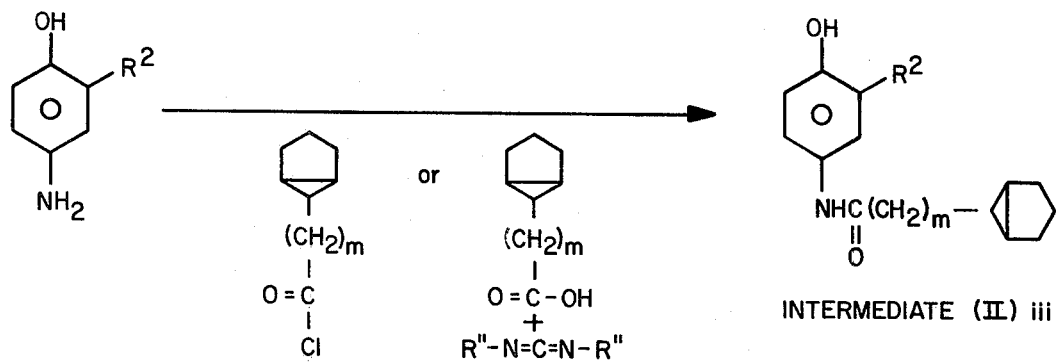
FIG_2
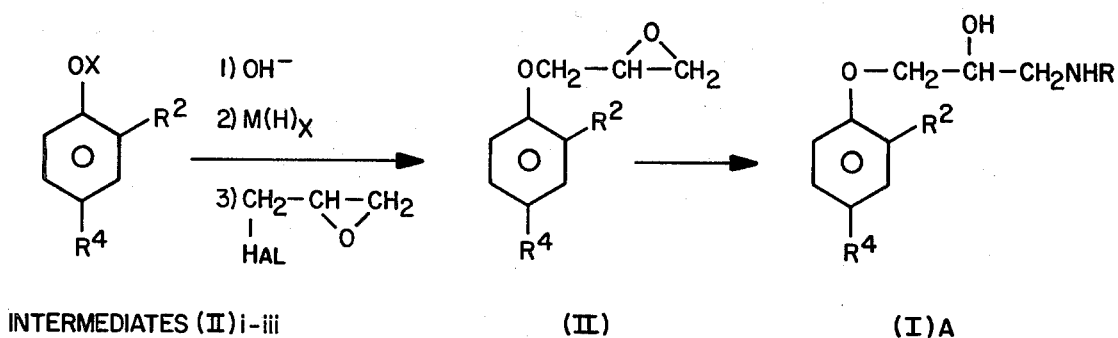
FIG_3
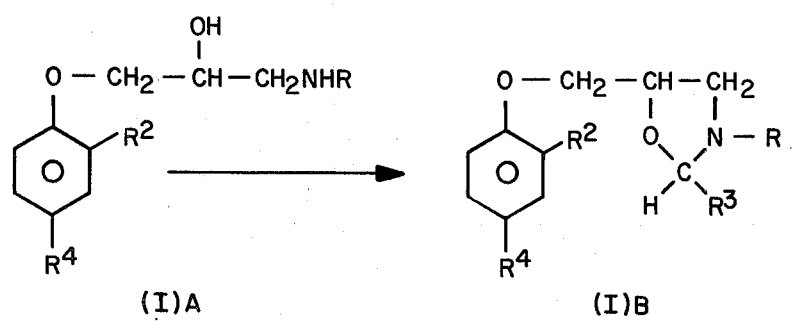
FIG_4

BICYCLO[3.1.0]HEXYL-SUBSTITUTED CARBONYLAMINOPHENOXY CARDIOVASCULAR AGENTS

FIELD OF THE INVENTION

This invention relates to 1-alkylamino-3-(4-[(endobicyclo[3.1.0]hex-6-yl)alkylureido]-1-phenoxy)-2-propanol and pharmaceutically acceptable salts thereof; to 1-alkylamino-3-(4-[(endobicyclo[3.1.0]hex-6-yl)alkylcarbonylamino]-1-phenoxy)-2-propanol and pharmaceutically acceptable salts thereof; to 1-alkylamino-3-(4-[(endobicyclo[3.1.0]-hex-6-yl)alkoxycarbonylamino]-1-phenoxy)-2-propanol and pharmaceutically acceptable salts thereof; and to methods of preparing such compounds. This invention further relates to 5-(4-[(endobicyclo[3.1.0]hex-6-yl)alkylureido]-1-phenoxy)methyl-3-alkyl-2-optionally substituted oxazolidine and to pharmaceutically acceptable salts thereof; to 5-(4-[(endobicyclo[3.1.0]hex-6-yl)alkylcarbonylamino]-1-phenoxy)methyl-3-alkyl-2-optionally substituted oxazolidine and to pharmaceutically acceptable salts thereof; to 5-(4-[(endobicyclo[3.1.0]hex-6-yl)alkoxycarbonylamino]-1-phenoxy)methyl-3-alkyl-2-optionally substituted oxazolidine and to pharmaceutically acceptable salts thereof and to methods for the preparation of these compounds. This invention also relates to pharmaceutical compositions comprising one or more of the above compounds and to methods for treating cardiac disorders and hypertension in mammals.

At the present time, the compound most frequently used in the United States for treatment of cardiac arrhythmias and hypertension is 1(isopropylamino)-3-(1-naphthoxy)-2-propanol (e.g. propranolol). Propranolol is believed to achieve its therapeutic action by competing with beta-adrenergic receptor stimulating agents for available beta receptor sites. When access to such sites is blocked by propanolol, the chronotropic, inotropic and vasodilator response to beta-adrenergic stimulation is decreased. Such activity, is however, not specific. Not only are heart muscle receptor sites affected, but lung and related organs are found to be influenced by this drug. Contraindication is therefore indicated for patients with bronchial asthma, allergic rhinitis, sinus brachycardia and the like.

In order to overcome the disadvantages present in the non-specific beta-adrenergic blocking agents, drugs specific for heart muscle blockage have been developed. See for example U.S. Pat. No. 3,408,387. One of the most active compounds of these selective beta-blockers is N-[4-(2-hydroxy-3-[(1-methylethyl)amino]-propoxy)]acetanilide, e.g. practolol. Unfortunately, this compound exhibits disadvantageous side effects in man. U.S. Pat. No. 3,897,441 discloses certain 3-(5-substituted aminocarbonylthiazol-2-yloxy)-2-propanol-1-amines and U,.S. patent application Ser. No. 796,342, filed July 19, 1976, now U.S. Pat. No. 4,101,770, discloses various 5-carbocyclic alkylaminocarbonyl-thiazol-2-yloxy compounds. Both these compound-types display beta-adrenergic blocking activity and cardiac selectivity. A novel analogous class of compounds having surprising beta-blocking activity, cardiac selectivity and reduced cardiac depression has now been discovered. These compounds are especially felicitous for the treatment or palliation of angina pectoris and cardiac arrhythmias and, because of their cardiac selectivity, can be safely applied to patients suffering from asthma or chronic lung disease.

SUMMARY

In summary, the compounds of the present invention can be represented by the generic formula

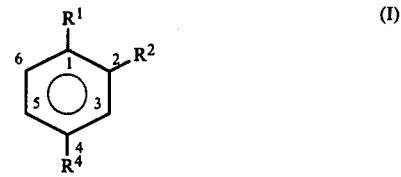

where $R^1$ is selected from the group

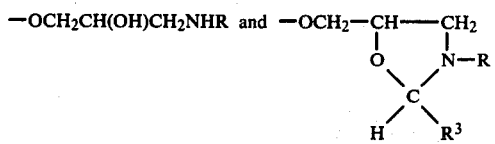

where R is $C_1$ to $C_4$ linear or branched alkyl; $R^2$ is selected from the group hydrogen, halo, nitrile, $C_1$ to $C_2$ alkyl, $C_1$ to $C_2$ alkoxy, acetyl and propanoyl; $R^3$ is hydrogen, $C_1$ to $C_4$ linear or branched alkyl or $C_6$ to $C_{10}$ carbocyclic aryl optionally substituted with halo, $C_1$ to $C_4$ linear or branched alkyl, $C_1$ to $C_4$ linear or branched alkoxy, $C_2$ or $C_4$ linear or branched acyl, $C_1$ to $C_4$ linear or branched carboalkoxy, nitrile or nitro; and $R^4$ is the group

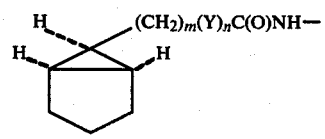

where Y is the radical -O- or

where $R^5$ is hydrogen or $C_1$ to $C_4$ linear or branched alkyl, n is the integer 0 or 1 and m is the integer 1 to 4.

The compounds in accordance with the present invention can be represented by the following sub-generic formula:

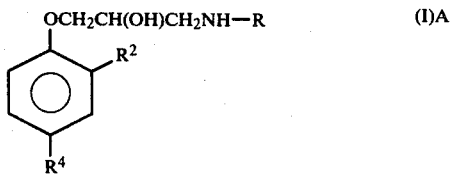

where R is $C_1$ to $C_4$ linear branched alkyl; $R^2$ is selected from the group hydrogen, halo, nitrile, $C_1$ to $C_2$ alkyl, $C_1$ to $C_2$ alkoxy, acetyl and propanoyl; and $R^4$ is the group

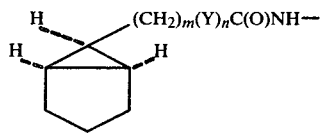

where Y is the radical -O- or

where $R^5$ is hydrogen or $C_1$ to $C_4$ linear or branched alkyl, n is the integer 0 or 1 and m is the integer 1 to 4.

The compounds in accordance with the present invention can be further represented by the following sub-generic formula:

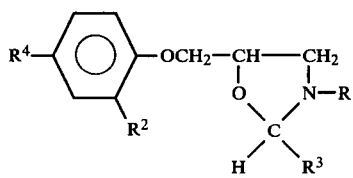
(I)B where R, $R^2$ and $R^4$ are defined above and where $R^3$ is hydrogen, $C_1$ to $C_4$ linear or branched alkyl or $C_6$ to $C_{10}$ carbocyclic aryl optionally substituted with halo, $C_1$ to $C_4$ linear or branched alkyl, $C_1$ to $C_4$ linear or branched alkoxy, $C_2$ to $C_4$ linear or branched acyl, $C_1$ to $C_4$ linear or branched carboalkoxy, nitrile or nitro.

Also encompassed within the present invention are pharmaceutically acceptable salts of the above compounds.

The compounds of the present invention of formula (I)A are prepared by treating the corresponding 1,2-epoxy-3-(4-[(endobicyclo[3.1.0]hex-6-yl)alkylureido, alkylcarbonylamino or alkoxycarbonylamino]-1-phenoxy)propane with an alkylamine having the desired alkyl substituents. Alternately, these compounds can be prepared by the hydrolysis of the corresponding compounds of the present invention of formula (I)B.

The process of the invention for preparing the compounds of formula (I)B comprises treating the compounds of formula (I)A with the desired $R^3$ aldehyde.

The pharmaceutical compositions of the present invention include solutions and solids or powders comprising one or more of the compounds in accordance with the present invention in combination with a suitable pharmaceutical solution, e.g. sterile water or pharmaceutically solid excipients.

A more detailed description of the present invention can be had by referring to the description of the preferred embodiments hereinbelow.

DESCRIPTION OF THE PREFERRED EMBODIMENTS

The compounds of the present invention can be represented by the following formula:

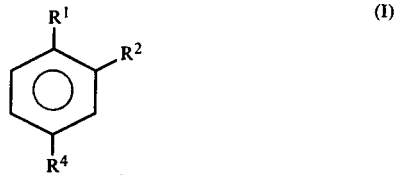
(I)

where $R^1$ is selected from the group

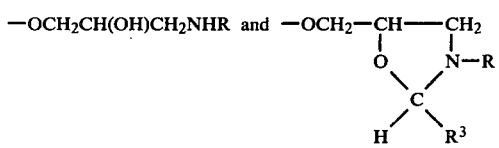

where R is $C_1$ to $C_4$ linear or branched alkyl; $R^2$ is selected from the group hydrogen, halo, nitrile, $C_1$ to $C_2$ alkyl, $C_1$ to $C_2$ alkoxy, acetyl and propanoyl; $R^3$ is hydrogen, $C_1$ to $C_4$ linear or branched alkyl or $C_6$ to $C_{10}$ carboxylic aryl optionally substituted with halo, $C_1$ to $C_4$ linear or branched alkyl, $C_1$ to $C_4$ linear or branched alkoxy, $C_2$ to $C_4$ linear or branched acyl, $C_1$ to $C_4$ linear or branched carboalkoxy, nitrile or nitro and $R^4$ is the group

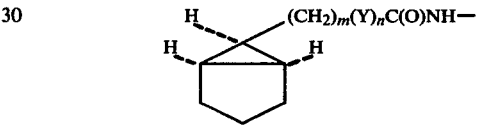

where Y is the radical -O- or

where $R^5$ is hydrogen or $C_1$ to $C_4$ linear or branched alkyl, n is the integer 0 or 1 and m is the integer 1 to 4.

The compounds of the present invention are more particularly represented by the formulas·

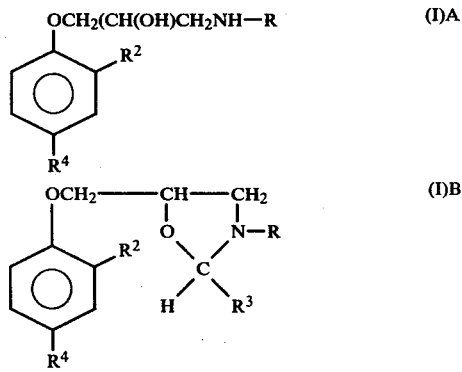

where R, $R^2$, $R^3$ and $R^4$ are as previously defined.

Preferably the group R is selected from methyl, ethyl, isopropyl, and t-butyl; most preferably isopropyl and t-butyl.

The substituent on the carbocylic aromatic ring, $R^2$ is preferably hydrogen, halo selected from the group chloro and fluoro, nitrile, methyl, ethyl, methoxy, ethoxy, acetyl or propanoyl.

In the case of $R^4$ having n equal to the integer 1, preferably m is the integer 1. In the compounds of formula (I)B, $R^3$ is preferably hydrogen, methyl or phenyl when $R^5$ is hydrogen or methyl, preferably hydrogen. When n is the integer 0, m is preferably the integer 2.

It should be emphasized that the above compounds of formula (I) bear the substituent endobicyclo[3.1.0]hex-6-yl attached either to an alkylureido, an alkylcarbonylamino or an alkoxycarbonylamino group, e.g. $R^4$ is

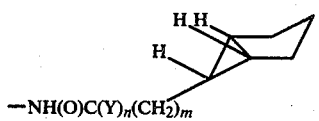

where Y, m and n are described above and where the open bond represents the point of attachment to the carbocyclic aromatic ring.

The pharmaceutically acceptable salts of the above compounds are also encompassed within the present invention.

The term "pharmaceutically acceptable salts" refers to those hydrogen anion addition salts which do not adversely affect the pharmaceutical properties of the parent compounds. With respect to the addition salts, suitable inorganic anions include, for example, chloride, bromide, iodide, sulfate, phosphate, nitrate and the like. Suitable organic anions include, for example, acetate, benzoate, lactate, picrate, propionate, butyrate, valerate, tartrate, maleate, fumarate, citrate, succinate, tosylate, ascorbate, nicotinate, adipate, gluconate and the like. Illustrations of the compounds of formula (I)A can be had by reference to the Examples.

The particularly preferred compounds of formula (I)A in accordance with the present invention are:

1-isopropylamino-3-(4-[2-(endobicyclo[3.1.0]hex-6-yl)-ethylureido]-1-phenoxy)-2-propanol;

1-t-butylamino-3-(4-[2-(endobicyclo[3.1.0]hex-6-yl)-ethylureido]-1-phenoxy)-2-propanol;

1-isopropylamino-3-(2-chloro-4-[2-(endobicyclo[3.1.0]-hex-6-yl)ethylureido]-1-phenoxy)-2-propanol;

1-t-butylamino-3-(2-chloro-4-[2-(endobicyclo[3.1.0]hex-6-yl)ethylureido]-1-phenoxy)-2-propanol;

1-isopropylamino-3-(4-[(endobicyclo[3.1.0]hex-6-yl)-methylureido]-1-phenoxy)-2-propanol;

1-t-butylamino-3-(4-[(endobicyclo[3.1.0]hex-6-yl)-methylureido]-1-phenoxy)-2-propanol;

1-isopropylamino-3-(2-chloro-4-[(endobicyclo-[3.1.0]-hex-6-yl)methylureido]-1-phenoxy)-2-propanol;

1-t-butylamino-3-(2-chloro-4-[(endobicyclo-[3.1.0]hex-6-yl)methylureido]-1-phenoxy)-2-propanol;

1-isopropylamino-3-(4-[(endobicyclo[3.1.0]hex-6-yl)-methyl-N-methylureido]-1-phenoxy)-2-propanol 1-t-butylamino-3-(4-[(endobicyclo[3.1.0]hex-6-yl)-methyl-N-methylureido]-1-phenoxy)-2-propanol 1-isopropylamino-3-(4-[2-(endobicyclo[3.1.0]hex-6-yl)-ethyl-N-methylureido]-1-phenoxy)-2-propanol;

1-t-butylamino-3-(4-[2-(endobicyclo[3.1.0]hex-6-yl)-ethyl-N-methylureido]-1-phenoxy)-2-propanol;

1-isopropylamino-3-(4-[2-(endobicyclo[3.1.0]hex-6-yl)-ethylcarbonylamino]-1-phenoxy)-2-propanol;

1-t-butylamino-3(4-[2-(endobicyclo[3.1.0]hex-6-yl)-ethylcarbonylamino]-1-phenoxy)-2-propanol;

1-isopropylamino-3(4-[(endobicyclo[3.1.0]hex-6-yl)-methoxycarbonylamino]-1-phenoxy)-2-propanol; and 1-t-butylamino-3(4-[(endobicyclo[3.1.0]hex-6yl)methoxy carbonylamino]-1-phenoxy)-2-propanol.

Typical illustrations of the compounds of formula I(B) can be had by reference to the Examples. The preferred $R^2$ substituents are isopropyl and t-butyl. $R^3$ is preferably hydrogen, methyl or phenyl optionally mono substituted with halo, $C_1$ to $C_2$ alkyl, $C_1$ to $C_2$ alkoxy, $C_2$ to $C_3$ acyl, $C_1$ to $C_2$ carboalkoxy, nitrile or nitro. The particularly preferred compounds of formula (I)B in accordance with the present invention are:

2-phenyl-3-t-butyl-5-(4-[2-(endobicyclo[3.1.0]hex-6-yl)ethylureido]-1-phenoxy)methyloxazolidine;

3-t-butyl-5-(4-[2-(endobicyclo[3.1.0]hex-6yl)ethylureido]-1-phenoxy)methyloxazolidine;

2-phenyl-3-isopropyl-5-(4-[(endobicyclo[3.1.0]hex-6-yl)methylureido]-1-phenoxy)methyloxazolidine;

3-t-butyl-5-(4-[(endobicyclo[3.1.0]hex-6-yl)methylureido]-1-phenoxy)methyloxazolidine;

3-isopropyl-5(4-[(endobicyclo[3.1.0]hex-6-yl)methyl-N-methylureido]-1-phenoxy)methyloxazolidine;

3-t-butyl-5(4-[(endobicyclo[3.1.0]hex-6-yl)methyl-N-methylureido]-1-phenoxy)methyloxazolidine;

3-isopropyl-5-(4-[2-(endobicyclo[3.1.0]hex-6-yl)ethyl-N-methylureido]-1-phenoxy)methyloxazolidine;

3-isopropyl-5-(4-[2-(endobicyclo[3.1.0]hex-6-yl)ethylcarbonylamino]-1-phenoxy)methyloxazolidine; and 3-isopropyl-5(4-[(endobicyclo[3.1.0]hex-6-yl)methoxycarbonylamino]-1-phenoxy)methyloxazolidine; and 3-t-butyl-5(4-[(endobicyclo[3.1.0]hex-6-yl)methoxycarbonylamino]-1-phenoxy)methyloxazolidine.

The preferred pharmaceutically acceptable salts are the hydrogen addition salts of the bromide, sulfate, lactate, tartrate, succinate and especially chloride and maleate. The preferred salts are the preferred anion addition salts of the compounds of formula (I)A or (I)B in accordance with the present invention and correspondingly the particularly preferred salts are the preferred hydrogen-anion addition salts of the preferred and the particularly preferred compounds herein, especially the hydrochloride and maleate salts.

The compounds in accordance with the present invention are conveniently prepared by applying the procedures discussed in the before referenced U.S. patent application Ser. No. 706,412 filed July 19, 1976, now U.S. Pat. No. 4,064,135, or by those procedures disclosed in U.S. patent application Ser. No. 846,953 filed Oct. 31, 1977, now U.S. Pat. No. 4,151,297, both incorporated herein by reference.

The objects of the present invention as disclosed will become more readily apparent from the following description in connection with the accompanying drawings in which:

FIG. 1 is the reaction sequence illustrative of the preparation of the intermediate compounds useful in preparing compounds of formula (I).

FIG. 2 is a further reaction sequence illustrative of the preparation of intermediate compounds useful in the preparation of compounds of formula (I).

FIG. 3 is a reaction sequence illustrative of the preparation of the compounds of the present invention of formula (I)A.

FIG. 4 is a reaction sequence illustrative of the conversion of the compounds of formula (I)A to those of formula I(B).

Briefly, the initial reaction sequence for the preparation of the compounds of formula (I)A where Y is the radical -O- or

where $R^5$ is hydrogen or $C_1$ to $C_4$ linear or branched alkyl, n is the integer 0 or 1 and m is the integer 1 to 4 is shown in FIG. 1. The starting materials illustrated in this Figure have a free phenolic group at the 1-position of the aromatic nucleus, i.e. (they are $R^2$-substituted hydroxybenzoic acids). This group is protected by group X (preferably a $C_2$ to $C_4$ linear or branched acyl halide or carboxylic acid anhydride), step (1). Reactions to protect such aromatic hydroxyl groups are well known to those skilled in the art. See Preparation 1 as an illustrative example. The compound thus formed is next converted to an isolable (but non-isolated) 4-isocyanate by first admixing the (protected) hydroxybenzoic acid with thionyl chloride in an aromatic solvent and heating for a time sufficient to form the acid chloride, typically for about 1 to 24 hours, preferably about 2 to 4 hours. An alkali metal azide such as sodium azide is then added to the acid chloride solution, step (2). Typically, the temperature of addition of such alkali metal azide is from −10° to 20°, preferably 0° to 5° for a time sufficient to form the 4-carbonylazide intermediate. Conversion of the carbonyl azide into the isocyanate is readily accomplished by heating such for 0.5 to about 2 hours, preferably about 1 hour. This reaction is the classical Curtius Rearrangement, the particulars of which being widely reported. See, for example, Chem. Revs. 43, 205 (1948). The isolable (but non-isolated) isocyanate is then reacted as shown in steps (3a) and (3b) with an endobicyclo[3.1.0]hex-6-yl-alkylene-N-optionally substituted amine or with an endobicyclo[3.1.0]hex-6-yl-alkanol to form the Intermediates (II)i and (II)ii, FIG. 1.

Intermediate (II)iii, FIG. 2, is prepared from an $R^2$-substituted 4-aminophenol by reacting such with an endobicyclo[3.1.0]hex-6-yl-alkylene carboxylic acid chloride. The starting amino compounds are conveniently prepared by hydrolysis of the isocyanate synthesized from the carbonyl azide as illustrated in FIG. 1, step (2) and summarized above. The hydrolysis occurs readily at room temperature over a period of time, typically about 30 minutes to about 2 hours, preferably about 60 minutes. The reaction of the aminophenol with the respective carboxylic acid chlorides, illustrated in FIG. 2 is typically conducted in an aromatic solvent at temperatures from about 20° to about 100°, preferably about 45° to 75°. In cases where the bicyclic alkylene carboxylic acid is used rather than the bicyclic alkylene acid chloride, it is preferable to have present in the reaction mixture a dehydrating agent to enhance the rate of reaction. Typical dehydrating agents are the carbodiimides such as dicyclohexylcarbodiimide.

The compounds in accordance with the present invention of formula (I)A are prepared from the above intermediates (II)i, (II)ii and (II)iii by the reaction scheme shown in FIG. 3. Intermediates (II)i-iii are first treated with strong base, such as aqueous sodium hydroxide to remove the protecting group X (FIG. 3, step 1.). The resulting phenol is then typically reacted with the metal hydride $M(H)_x$ where x is the valence of metal M (FIG. 3, step 2.). This initial treatment is typically conducted at temperatures in the range of from about −30° to 30°, preferably about from −10° to 5° for about from one minute to one hour, preferably from about five minutes to 20 minutes. An epihalohydrin such as epibromohydrin or epichlorohydrin, typically dissolved in an inert organic solvent, is then added to the preceding mixture (FIG. 3, step 3.). Typically, this treatment is conducted at temperatures in the range of from about 20° to 75°, preferably from about 25° to 45°, for from about one minute to three hours, preferably from about 10 to 30 minutes. Typically, mole ratios of metal hydride:phenol (the compound of the FIG. 3, step 1.) of about from 1 to 5:1 are used, preferably about from 1.0 to 1.3:1, and mole ratios of the compound of the FIG. 3, step 2. (reaction not shown):epihalohydrin in the range of about from 1 to 5:1, preferably from about 1.0 to 1.3:1 are used. Suitable metal hydrides which can be used include, for example, sodium hydride, potassium hydride, lithium hydride and the like. Suitable inert organic solvents of use include, for example, tetrahydrofuran, diethyl ether, dioxane, dimethoxyethane, dimethylformamide and the like and mixtures thereof. Both procedures of the treatment are conducted under anhydrous conditions and preferably under an inert atmosphere (e.g. nitrogen). Compound (II) is preferably isolated before being used as starting material for the next step. Such isolation can be effected by conventional separation procedures such as, for example, precipitation with water, extraction, crystallization or chromatography. Specific illustrations of typical separation and isolation procedures can be had by reference to the appropriate Preparations, hereinbelow.

The compounds of formula (I)A can be conveniently prepared by treating compound (II) with a monoalkylamine having the desired alkyl substituent. Typically, this treatment is carried out in an inert organic solvent and is typically conducted at temperatures in the range of about from −10° to 100°, preferably about from 10° to 50°, for about from one hour to 48 hours, preferably about from three to 18 hours. Typically, a mole ratio of alkylamine: compound (II) in the range of from about 1 to 30:1, preferably from about 1 to 10:1, is used. Suitable alkylamines which can be employed include, for example, methylamine, ethylamine, isopropylamine, t-butylamine and the like. Suitable inert organic solvents which can be used include, for example, methanol, ethanol, monoglyme and the like and mixtures thereof. The resulting products of formula (I)A can then be separated and isolated according to conventional separation procedures such as, for example, evaporation, crystallization, chromatography, thin-layer chromatography, etc. Specific illustrations of typical separation and isolation procedures can be had by reference to the corresponding Examples, set forth hereinbelow.

The compounds of formula (I)B can be prepared directly from the corresponding compounds of formula (I)A by the procedure illustrated in FIG. 4.

This preparation can be conveniently effected by reacting the corresponding compound of formula (I)A with an aldehyde having the desired $R^3$ substituent. The reaction can be carried out by treating the compound of formula (I)A with the desired aldehyde using a low molecular weight alkanol (e.g. ethanol) as solvent. Typically a mole ratio of about from 1 to 10 moles of aldehyde is used per mole of compound of formula (I)A. The reaction is typically conducted at temperatures in the range of about from 20° to 140° for about from 1 to 48 hours. Suitable aldehydes which can be used include, for example formaldehyde, acetaldehyde, benzaldehyde, p-acetylbenzaldehyde, p-cyanobenzaldehyde, p-chlorobenzaldehyde, p-carbomethoxybenzaldehyde and the like. In some cases, a strong base is desirably present in the reaction mixture such as aluminum isopropoxide and the like. Alternately, these compounds are prepared by heating a mixture of the desired $R^3$ aldehyde and the compounds of formula (I)A in an inert organic solvent such as benzene, toluene, etc. and azeotropically removing water.

The product of formula (I)B can be separated and purified according to conventional procedures such as, for example, illustrated in the Examples, hereinbelow. Care should be exercised during the purification procedure as the compounds of formula (I)B are easily hydrolyzed to the compounds of formula (I)A under both acid and basic conditions. The alkylamino compounds of formula (I)A can be readily prepared by simple acid or base hydrolysis of the corresponding compounds of formula (I)B. Acid hydrolysis can be conveniently effected by treating the compound of formula (I)B with a suitable organic acid such as, for example, acetic acid, formic acid, oxalic acid and the like or a suitable inorganic acid such as, for example, hydrochloric acid, sulfuric acid and the like. Preferably this hydrolysis is conducted under mildly acidic conditions. Similarly, basic hydrolysis can be conducted by treating the compound of formula (I)B with a suitable base such as, for example, sodium hydroxide. Preferably this hydrolysis is conducted under mildly alkaline conditions. Alternatively, the hydrolysis can be conducted via exchange with a suitable ion exchange resin in either the $H^+$ or $OH^-$ form.

The pharmaceutically acceptable acid addition salts of the compounds of formulas (I)A and (I)B can be prepared from the parent compound via careful neutralization with the desired acid. Other pharmaceutically acceptable addition salts can then be conveniently prepared from the addition salts via anion exchange with a suitable ion exchange resin in the desired anionic form.

The compounds of the invention are useful in the treatment and palliation of cardiovascular abnormalities in mammals. These compounds primarily achieve their therapeutic action by selectively blocking the cardiac beta-adrenergic receptor sites and, accordingly, because they are cardiac selective, they can also be applied to treat cardiac abnormalities in patients suffering from asthma or chronic obstructive lung disease.

The compounds are especially useful in the treatment or palliation of cardiac arrhythmias, angina pectoris, hypertrophic subaortic stenosis, pheochromocytoma, thyrotoxicosis, hyperkenetic syndromes, tetralogy of Fallot, mitral stenosis with tachycardia, general ischemic conditions and hypertension founded on elevated cardiac outputs due to a hyperadrenergic state. The compounds are active, both in the treatment or palliation of acute attacks of such cardiac disorders, and further can be applied prophylactically to prevent or reduce the frequency of such attacks. This prophylactic action is particularly desirable in reducing the frequency of attacks of angina pectoris, since the medication presently commonly used (i.e., nitroglycerin) in the treatment of angina pectoris has no recognized prophylactic action. Additional information concerning the use, action and determination of beta-blockers can be obtained by reference to the literature such as, for example, Dotlery et al, *Clinical Pharmacology and Therapeutics*, Volume 10, No. 6, 765–797 and the references cited therein.

The compounds of the invention are also useful in the treatment of hypertension in mammals.

The compounds of this invention are typically administered, both for the treatment of cardiac disorders and hypertension, in dosages of about from 0.01 to 5 mg per kg. of body weight. The precise effective dosage will, of course, vary depending upon the mode of administration, the condition being treated and the host. Where the compounds are used to treat cardiac conditions such as arrhythmias, the compounds are typically administered either orally or intraveneously. Where the compounds are administered to treat hypertension or cardiac conditions such as angina pectoris, the compounds are, for the sake of convenience, typically administered orally.

The compounds of the invention can be administered for the treatment of cardiac disorders and hypertension in a wide variety of dosage forms, either alone or in combination with other pharmaceutically compatible medicaments, in the form of pharmaceutical compositions suited for oral or parenteral administration. The compounds are typically administered as pharmaceutical compositions consisting essentially of the compounds of the invention and a pharmaceutical carrier. In the case of the compounds of formula (I)A, the compounds are typically administered as pharmaceutically acceptable salts. The pharmaceutical carrier can be either a solid material or liquid, in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups or elixirs and optionally can contain small quantities of preservatives and/or buffering agents, and preferably contain the therapeutic agents in convenient unit dosage concentrations.

The solid compositions can take the form of tablets, powders, capsules, pills or the like, preferably in unit dosage forms for simple administration or precise dosages. Suitable solid cariers include, for example, pharmaceutical grades of starch, lactose, sodium saccharin, sodium bisulfite and the like.

Also based on studies on related compounds, it can be predicted that a number of the present compounds will exhibit useful local anesthetic activity. Where the compounds are applied as local anesthetics, they can be administered topically, intradermally or subcutaneously.

A further understanding of the invention can be had from the following non-limiting Preparation and Examples. Also as used hereinabove and below unless expressly stated to the contrary, all temperatures and temperature ranges refer to the Centigrade system and the terms ambient or room temperature refer to about 20° C. The term percent or (%) refers to weight percent and the term mole or moles refers to gram moles. The term "equivalent" refers to a quantity of reagent equal in moles to the moles of the preceding or succeeding reactant recited in that Preparation or Example in the terms of moles or finite weight or volume. Proton or [13]carbon nuclear magnetic rsonance spectra (NMR and $^{13}$C NMR) are determined at 100, 90, or 60 MHz (the signs of the coupling constants are not assigned) and signals are assigned as singlets (s), broad singlets (bs)

doublets (d), double doublets (dd), triplets (t), double triplets (dt), quartets (q) and multiplets (m) and reported using the delta scale from tetramethylsilane (internal standard) unless as otherwise noted. Compounds having assymetric centers and optical activity are isolated in their racemic form (±) unless otherwise indicated. The compounds of formula (I) exist as pairs of enantiomers. Each enantiomer or optical isomer as well as mixtures thereof are included within the present invention. The compounds of formula (I) which exist as pairs of enantiomers can be administered as racemic mixtures or they can be administered as resolved enantiomers. In some instances, one enantiomer exhibits greater antiarrhythmic activity, is more cardiac selective, etc. than the other corresponding enantiomer.

PREPARATION 1

(Endobicyclo[3.1.0]hex-6-yl)methylamine (a) To 10 g. of (endobicyclo[3.1.0]hex-6-yl)methanol [(JACS 85, 582 (1963)] in 60 ml. of dry ether, at 5°, 12 g. of phosphorous tribromide are added over 3 minutes. After 15 minutes of reaction time, ice water is added (to the ether solution) and the ether solution is washed several times with water.

(b) To a solution of 7.0 g. of sodium azide in 100 ml. dimethylsulfoxide (DMSO) and 5 ml. water, at 5°, (endobicyclo[3.1.0]hex-6-yl)methyl bromide, from a), in 10 ml. DMSO is added. The mixture is stirred at 5° for 45 minutes and at 70° for one hour. Thereafter, the reaction mixtue is diluted with ice water and (endobicyclo[3.1.0]-hex-6-yl)methyl azide is extracted with 100 ml. of hexane. The hexane layer is washed several times with water, the solution dried over magnesium sulfate and, after filtering, hexane is evaporated from the solution under reduced pressure.

(c) To a refluxing suspension of 3.0 g. of lithium aluminum hydride (LAH) in 150 ml. of ether, the azide of step (6) in 50 ml. of ether is added dropwise over one hour. The solution is then cooled to 5°, and water is added dropwise to destroy excess of LAH. The ether solution is dried over sodium sulfate and filtered. After evaporation of the ether, (endobicyclo[3.1.0]hex-6-yl)-methylamine is distilled bulb to bulb (40 mm).

PREPARATION 2

3-(Endobicyclo[3.1.0]hex-6-yl)propionic acid

To 6.6 g. of diisopropylamine in 50 ml. tetrahydrofuran (THF) at −78°, under nitrogen, 44 ml. of butyl lithium in hexane are added. To this solution, at −20°, 2.0 g. of acetic acid are added and the mixture is allowed to stand at room temperature for 30 minutes [J. Org. Chem. 37, 451 (1972)]. The mixture is diluted with 4 ml. of hexamethylphosphorous triamide and, at 5°, 2-(endobicyclo[3.1.0]hex-6-yl)ethyl bromide [prepared from 3.0 g. (endobicyclo[3.1.0]hex-6-yl)methanol, see Preparation 1,step (a)] are added. The mixture is stirred at room temperature for 1 ½ hours. Thereafter tetrahydrofuran is distilled under reduced pressure. After acidification of the mixture with 6 n hydrochloric acid, 3-(endobicyclo[3.1.0]-hex-6-yl)propionic acid is extracted with 2×100 ml. of ether. The ether layer is washed with water and extracted with 10% sodium hydroxide (80 ml.). The aqueous layer is washed with 2×100 ml. ether and, after acidification of this basic layer, with (6N hydrochloric acid) extracted with ether, is dried over magnesium sulfate, filtered and the solvent evaporated, yielding 2.0 g. of the captioned compound.

PREPARATIN 3

Methyl-2-(endobicyclo[3.1.0]hex-6-yl)ethylamine (a) To 8.0 g. of 2-(endobicyclo[3.1.0]hex-6-yl)-ethylamine at 5°, 15 ml. of formic acid (98%9 is added, followed by the addition of 15 ml. of acetic anhydride. The mixture is stirred at 50° for 1 hour and thereafter poured into crushed ice. After washing in succession with water (2×75 ml.), aqueous sodium bicarbonate (5%), water and filtering, the ether extract is chromatographed over silica gel, giving 3.5 g. N-[2-(endobicyclo[3.1.0]hex-6-yl)ethyl]formamide.

(b) The LAH (1.5 g.) reduction of the formamide of step (a) is carried out as shown in Preparation 1, step (c), affording 3.0 g. methyl-2-(endobicyclo[3.1.0]hex-6-yl)-ethylamine.

PREPARATION 4

2-Chloro-4-(3-endobicyclo[3.1.0]hex-6-yl-propanoylamino)-phenol

A solution of 1.5 g of 3-(endobicyclo[3.1.0]hex-6-yl)propanoic acid in 10 ml of thionyl chloride is refluxed for 30 minutes. Thereafter all of excess thionyl chloride is distilled under reduced pressure. A solution of this 3-endobicyclo[3.1.0]hex-6-yl-propanoyl chloride in 10 ml methylene chloride is added to a suspension of 2-chloro-4-amino phenol [J.A.C.S. 45, 2192 (1923)], 1.4 g., in 50 ml of tetrahydrofuran, 50 ml of methylene chloride and 4 ml of triethylamine at 5°. The mixture is stirred for three minutes and refluxed for 30 minutes. Thereafter the solvents are evaporated under reduced pressure and the residue dissolved in ethyl acetate. After washing the ethyl acetate layer in succession with water, 10% aqueous hydrochloric acid, water, 5% aqueous sodium bicarbonate and water, the solvent is evaporated. The mixture is applied to preparative plates, affording 1.1 g. of 2-chloro-4-(3-enbodicyclo[3.1.0]hex-6-yl-propanoylamino)-1-phenol.

PREPARATION 5

4-Acetoxybenzoic acid

To 20 g. of 4-hydroxybenzoic acid in suspension in 150 ml. of tetrahydrofuran (THF) and 150 ml. methylene chloride, 35 g. of triethylamine, 35 g. of acetic anhydride and 3 g. of 4-dimethylaminopyridine are added and the mixture refluxed for 30 minutes. The solvents are thereafter evaporated under reduced pressure and 6N hydrochloric acid is added to the residue. The resulting slurry is filtered, washed with water and dried, affording 20 g. of the captioned compound.

PREPARATION 6

(a) 4-Acetoxy-[2-(endobicyclo[3.1.0]hex-6-yl)ethyl]phenyl urea, and (b) 4-Hydroxy-[2-(endobicyclo[3.1.0]hex-6-yl)ethyl]-phenyl urea A solution (20 ml.) of thionyl chloride containing 3.0 g of 4-acetoxybenzoic acid (Preparation 5) is refluxed for 3 hours. After evaporation of excess thionyl chloride, 4-acetoxybenzoyl chloride is obtained and dissolved in 15 ml. THF and 15 ml. acetone at 5°. This solution is added over 30 minutes to 2 g. of sodium azide in 10 ml. of water. The mixture is extracted with 2×75 ml. of toluene and the toluene solution washed several times with water. After drying the toluene solution containing the 4 acetoxybenzoyl azide with anhydrous magnesium sulfate, the mixture is filtered and the filtrate refluxed for one hour. The resulting 4-acetoxyphenyl isocyanate, in toluene, is cooled to 5° and reacted with 2.2 g. of 2-(endobicyclo[3.1.0]hex-6-yl)ethylamine. The product is a mixture of 4-acetoxy-[2-(endobicyclo[3.1.0]hex-6-yl)-ethyl]phenylurea and 4-hydroxy-[2-(endobicyclo[3.1.0]hex-6-yl)phenylurea in a ratio of 1:1. This mixture, in a solution of 50 ml. of methanol, is reacted with 10 ml. of a solution of 10% aqueous sodium hydroxide at 60° for 15 minutes. The resulting solution is then acidified with 6N hydrochloric acid. This mixture is extracted into 150 ml. of methylene chloride ($CH_2Cl_2$) and this extract washed with water, dried over magnesium sulfate and filtered. After chromatographing over silica gel, 1.7 g. of 4-hydroxy[2-(endobicyclo[3.1.0]hex-6-yl)ethyl]phenylurea are isolated.

PREPARATION 7

(a) 1-Acetoxybenzoylchloride

A solution of 4-acetoxybenzoic acid (3g.) in thionyl chloride (30mls.) is refluxed under argon for 5 hours. Excess thionyl chloride is remmoved in vacuo to yield 3.5g. of 1-acetoxybenzoyl chloride.

(b) Acetoxy-4-[(endobicyclo[3.1.0]hex-6-yl)methoxycarbonylamino]benzene

To an ice cold solution of the acid chloride of step a) (9.6g) in 50% dry tetrahydrofuran/acetone (45 mls. of each) is added slowly, with stirring under argon, sodium azide (9g.) in water (33mls.) (reaction is complete, by TLC, in 30 minutes). Solvents are removed in vacuo, the balance of reaction poured into water and the product extracted into toluene. The latter is washed with water, brine, dried over magnesium sulfate, filtered, and concentrated to half its volume. To this solution is added endobicyclo[3.1.0]hex-6-ylmethanol (6.0g.) and the resultant refluxed for 2 hours. Toluene is removed in vacuo. The product is separated by silica gel chromatography eluting the product with 75–100% ether/hexane to yield 13.9g. of crystalline 1-acetoxy-5-[endobicyclo[3.1.0]hex-6-yl)methoxycarbonylamino]benzene m.p. 94.5°.

(c) 4-[(endobicyclo[3.1.0]hex-6-yl)methoxycarbonylamino]-phenol.

A solution of the compound produced in step (b) (9.0g.) in 3% methanolic potassium hydroxide (26 mls.) is hydrolyzed to the phenol by stirring at room temperature for 45 minutes. The reaction is diluted with water, acidified with 2N hydrochloric acid and the product extracted into ether. The latter is wahsed with water, brine, dried over magnesium sulfate, filtered, and evaporated to dryness to yield 68% of crystalline 4-[(endobicyclo[3.1.0]-hex-6-yl) methoxycarbonylamio]-phenol m.p. 92°–94°.

PREPARATION 8

1,2-Epoxy-3-(4-[2-(endobicyclo[3.1.0]hex-6-yl)ethylureido]-1-phenoxy)propane

A mixture consisting of 1.6 g. of 4-hydroxy-[2-(endobicyclo[3.1.0]hex-6-yl)ethyl]phenylurea bicyclo[3.1.0]hex-6-yl)ethyl]phenylurea (Preparation 6b), 3.1 g. of sodium carbonate, 8.0 g. of epibromohydrin, 15 ml. of water and 150 ml. of methanol is reacted at 70°for 3 hours. Thereafter the methanol is evaporated under reduced pressure. Additional water (30 ml.) is added to the mixture and 1,2-epoxy-3-(4-[2-(endobicyclo[3.10-]hex-6-yl)ethylureido]-1-phenoxy)propane is extracted with methylene chloride (150 ml.). This extract is washed with water, dried over magnesium sulfate, filtered and applied to silica gel preparative plates, affording 1.1 g. of 1,2-epoxy-3-(4-[2-(endobicyclo[3.1.0]hex-6-yl)ethylureido]-1-phenoxy)propane, m.p. 89–90°.

Similarly, by following the same procedure above but using other substituted phenols, the following compounds are prepared:

1,2-epoxy-3-(2-acetyl-4-[2-(endobicyclo[3.1.0]hex-6-yl)ethylaminocarbonyl]-1-phenoxy)propane;

1,2-epoxy-3-(4-[(endobicyclo[3.1.0]hex-6yl)methylureido]-1-phenoxy)propane, m.p. 145–147°;

1,2-epoxy-3-(2-chloro-4-[2-(endobicyclo[3.1]hex-6-yl)ehtyl-N-methylureido]-1-phenoxy)propane, oil;

1,2-epoxy-3-(4-[2-(endobicyclo[3.1.0]hex-6-yl)ethyl-N-methylureido]-1-phenoxy)propane, oil;

1,2-epoxy-3-(2-cyano-4-[2-(endobicyclo[3.1.0]hex-6-yl)-ethylaminocarbonyl]-1-phenoxy)propane;

1,2-epoxy-3-(2-chloro-4-[2-(endobicyclo[3.1.0]hex-6-yl)ethylureido]-1-phenoxy)propane;

1,2-epoxy-3-(2-chloro-4-[2-(endobicyclo[3.1.0]hex-6-yl)ethylcarbonylamino]-1-phenoxy)propane, m.p. 83–84°;

1,2-epoxy-3-(4-[2-(endobicyclo[3.1.0]hex-6yl)ethylcarbonylamino]-1-phenoxy)propane;

1,2-epoxy-3-(2-chloro-4-[3-(endobicyclo[3.1.0]hex-6-yl)propoxycarbonylamino]-1-phenoxy)propane;

1,2-epoxy-3-(2-acetyl-4-[2-(endobicyclo[3.1.0]hex-6-yl)ethylcarbonylamino]-1-phenoxy propane; and 1,2-epoxy-3-(4-[(endobicyclo[3.1.0]hex-6-yl)methoxycarbonylamino]-1-phenoxy)propane, m.p. 73–74.5°.

EXAMPLE 1

This illustrative of the process for preparing the compounds of the present invention.

(±) 1-isopropylamino-3-(4-[2-(endobicyclo[3.1.0-]hex-6-yl)ethylureido]-1-phenoxy)-2-propanol.

To a solution of 10 g. of 1,2-epoxy-3-(4-[2-(endobicyclo[3.1.0]hex-6-yl)ethylureido]-1-phenoxy)propane (Preparation 7) in 20 ml. of methanol is added 5 ml. of isopropylamine. The mixture is stirred at room temperature for 20 hours. The propanol product is isolated via preparative TLC plates, giving 910 milligrams, m.p. 102–104°.

Using other epoxides illustrated in Preparation 7, the following propanol products are prepared in the manner similar to that disclosed above, utilizing isopropylamine and t-butylamine respectively. All compounds are isolated in the racemic (±) form:

1-t-butylamino-3-(4-[2-(endobicyclo[3.1.0]hex-6-yl)-ethylureido]-1-phenoxy)-2-propanol;

1-isopropylamino-3-(2-acetyl-4-[2-(endobicyclo[3.1.0]-hex-6-yl)ethylureido]-1-phenoxy)-2-propanol;

1-t-butylamino-3-(2-acetyl-4-[2-(endobicyclo[3.1.0-]hex-6-yl)ethylureido]-1-phenoxy)-2-propanol;

1-isopropylamino-3-(4-[(endobicyclo[3.1.0]hex-6yl)-methylureido]-1-phenoxy)-2-propanol, m.p. 91–93°;

1-t-butylamino-3-(4-[(endobicyclo[3.1.0]hex-6-yl)-methylureido]-1-phenoxy)-2-propanol, m.p. 99–101°;

1-isopropylamino-3-(2-chloro-4-[2-(endobicyclo[3.1.0]-hex-6-yl)ethyl-N-methylureido]-1-phenoxy)-2-propanol, m.p. 77–78°;

1-t-butylamino-3-(2-chloro-4-[2-(endobicyclo[3.1.0]-hex-6-yl)ethyl-N- methylureido]-1-phenoxy)-2-propanol;

1-isopropylamino-3-(4-[2-(endobicyclo[3.1.0]hex-6-yl)-ethyl-N-methylureido]-1-phenoxy)-2-propanol, m.p. 125–126°;

1-t-butylamino-3-(4-[2-(endobicyclo[3.1.0]hex-6-yl)-ethyl-N-methylureido]-1-phenoxy)-2-propanol, m.p. 125–126°;

1-isopropylamino-3-(2-cyano-4-(endobicyclo[3.1.0]hex-6-yl)ethylureido]-1-phenoxy)-2-propanol;

1-t-butylamino-3-(2-cyano-4-[2-(endobicyclo[3.1.0-]hex-6-yl)ethylureido]-1-phenoxy)-2-propanol;

1-isopropylamino-3-(2-chloro-4-[2-(endobicyclo[3.1.0]-hex-6-yl)ethylureido]-1-phenoxy)-2-propanol;

1-t-butylamino-3-(2-chloro-4-[2-(endobicyclo[3.1.0]-hex-6-yl)ethylureido]-1-phenoxy)-2-propanol;

1-isopropylamino-3-(4-[2-(endobicyclo[3.1.0]hex-6-yl)-ethylcarbonylamino]-1-phenoxy)-2-propanol, m.p. 115–117°;

1-t-butylamino-3-(4-[2-(endobicyclo[3.1.0]hex-6-yl)-ethylcarbonylamino]-1-phenoxy)-2-propanol;

1-isopropylamino-3-(2-acetyl-4-[2-(endobicyclo]3.1.0]-hex-6-yl)ethylcarbonylamino]-1-phenoxy)-2-propanol;

1-t-butylamino-3-(2-acetyl-4-[2-(endobicyclo[3.1.0-]hex-6-yl)ethylcarbonylamino]-1-phenoxy)-2-propanol;

1-isopropylamino-3-(2-chloro-4-[2-(endobicyclo[3.1.0]-hex-6-yl)ethylcarbonylamino]-1-phenoxy)-2-propanol, m.p. 131–133°;

1-t-butylamino-3-(2-chloro-4-[2-(endobicyclo[3.1.0]-hex-6-yl)ethylcarbonylamino]-1-phenoxy)-2-propanol;

1-isopropylamino-3-(4-[(endobicyclo[3.1.0]hex-6-yl)-methoxycarbonylamino]-1-phenoxy)-2-propanol, m.p. 101–102°; and 1-t-butylamino-3-(4-[(endobicyclo[3.1.0]hex-6-yl)-methoxycarbonylamino]-1-phenoxy)-2-propanol, m.p. 136–137°.

EXAMPLE 2

This Example illustrates methods of preparing hydrochloride addition salts of the compounds of formula (I)A. In this example 1 g. of 1-isopropylamino-3-(4-[2-(endobicyclo[3.1.0]hex-6-yl)ethylureido]-1-phenoxy)-2-propanol is dissolved in 10 ml. of ethyl ether at 20° C. A stream of gaseous anhydrous hydrogen chloride is passed over the surface of the solution until the supernatent liquid becomes colorless. The resulting precipitate is collected by filtration, washed with ethyl ether and then crystallized from methanol/diethyl ether, affording crystalline 1-isopropylamino-3-(4-[2-(endobicyclo[3.1.0]-hex-6-yl)-ethylureido]-1-phenoxy)-2-propanol hydrochloride.

Similarly, by following the same procedure, the corresponding hydrochloride addition salts of each of the products of Example 1 are respectively prepared.

EXAMPLE 3

This example illustrates methods of preparing the maleate addition salts of compounds of formula (I)A. In this example, one gram of 1-isopropylamino-3-(4-[2-(endobicyclo[3.1.0]hex-6-yl)ethylureido]-1-phenoxy)-2-propanol is dissolved in 5 ml. of ethyl acetate at 20° C. To this solution is added 10 ml. of a saturated solution of maleic acid in ethyl ether. The mixture is allowed to stand for one hour at room temperature. The resulting precipitate is recovered by filtration, washed three times with ethyl ether and then crystallized from a mixture of ethyl ether and ethanol (10:1) affording crystalline 1-isopropylamino-3-(4-[2-(endobicyclo[3.1.0-]hex-6-yl)ethylureido]-1-phenoxy)-2-propanol maleate.

Similarly, by following the same procedure, the corresponding maleate salts of each of the products of Example 1 are prepared.

EXAMPLE 4

This Example illustrates the method of converting the compounds of formula (I)A into the corresponding compounds of formula (I)B. In this Example, 1 mmole of 1-isopropylamino-3-(4-[2-(endobicyclo[3.1.0]hex-6-yl)ethylureido]-1-phenoxy)-2-propanol in 10 ml. of methanol is admixed with 20 ml. of acetaldehyde and 2 g. of aluminum isopropoxide and stirred at room temperature for one hour. The solvent is removed by evaporation under vacuum, affording 2-methyl-3-isopropyl-5-(4-[2-(endobicyclo[3.1.0]hex-6-yl)ethylureido]-1-phenoxy)methyloxazolidine.

Similarly by following the same procedure but using other aldehydes in place of acetaldehyde, the corresponding 2-substituted-3-isopropyl oxazolidine homologs of the above products are respectively prepared.

By replacing the above compounds of formula (I)A with other formula (I)A compounds, the compounds of formula (I)B can be prepared with various 3-substitutions on the oxazolidine ring.

EXAMPLE 6

This Example illustrates the method of converting the compounds of formula (I)B into the compounds of formula (I)A of the invention. In this Example, 1 g. of 2-phenyl-3-t-butyl-5-(4-[2-(endobicyclo[3.1.0]hex-6-yl)ethylureido]-1-phenoxy)methyloxazolidine is dissolved in 50 ml. of ethanol and this solution is treated with aqueour 5% sodium hydroxide (20 ml.) at 20°. The mixture is allowed to stand, with intermittant shaking, for 0.5 hours, the organic layer is extracted with methylene chloride, washed three times with water, dried over magnesium sulfate and then evaporated to dryness affording 1-t-butylamino-3-(4-[2-(endobicyclo[3.1.0-]hex-6yl)ethylureido]-1-phenoxy)-2-propanol.

Similarly, by following the same procedure, the compounds of formula (I)B, i.e., the products illustrated in Example 4, are respectively hydrolyzed to the corresponding compounds of formula (I)A.

EXAMPLE 6

This Example illustrates an alternate method for converting the compounds of formula (I)B to the compounds of formula (I)A. In this example 1 g. of 2-phenyl-3-t-butyl-5-(4-[2-(endobicyclo[3.1.0]hex-6-yl)ethylureido]-1-phenoxy)methyloxazolidine is dissolved in 20 ml. of methanol containing 4 ml. of 5% aqueous hydrochloric acid at 20%. After 30 minutes, the mixture is neutralized with dilute aqueous sodium carbonate solution, poured into water and extracted with ethyl acetate. The ethyl acetate extract is evaporated to dryness yielding 1-t-butylamino-3-(4-[2-(endobicycly[3.1.0-]hex-6-yl)ethylureido]-1-phenoxy)-2-propanol.

Similarly, by following the same procedure, the compounds of formula (I)B,. i.e., the products illustrated in Example 4, are respectively hydrolyzed to the corresponding compounds of formula (I)A.

Many modification and variations of the invention described herein can be made without departing from the essence and scope thereof. The described embodiments are to be considered in all respects only as illustrative and not restrictive and the scope of the invention is, therefore, indicated by the appended claims rather than the foregoing description. All changes which come within the meaning and range of the claims are to be embraced within their scope.

What is claimed is:

1. A compound of the formula

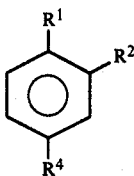  (I)

wherein $R^1$ is selected from the group

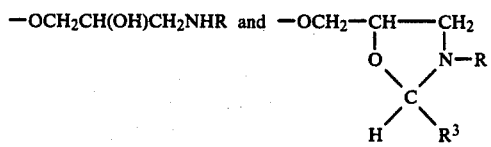

and R is $C_1$ to $C_4$ linear or branched alkyl; $R^2$ is selected from the group hydrogen, halo, nitrile, $C_1$ to $C_2$ alkyl, $C_1$ to $C_2$ alkoxy, acetyl and propanoyl; $R^3$ is hydrogen, $C_1$ to $C_4$ linear or branched alkyl or $C_6$ to $C_{10}$ carbocyclic aryl optionally substituted with halo, $C_1$ to $C_4$ linear or branched alkyl, $C_1$ to $C_4$ linear or branched alkoxy, $C_2$ to $C_4$ linear or branched acyl, $C_1$ to $C_4$ linear or branched carboalkoxy, nitrile or nitro; and $R^4$ is the group

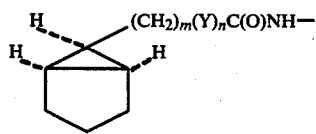

where Y is the radical

where $R^5$ is hydrogen or $C_1$ to $C_4$ linear or branched alkyl, n is the integer 0 or 1 and m is the integer 1 to 4 and pharmaceutically acceptable salts thereof.

2. The compound of claim 1 wherein $R^1$ is

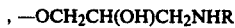

wherein R is defined above and pharmaceutically acceptable salts thereof.

3. The compound of claim 2 wherein R is selected from the group isopropyl and t-butyl.

4. The compound of claim 3 wherein R is isopropyl, m is the integer 2 and n is the integer 0.

5. The compound of claim 4 wherein $R^2$ is selected from the group hydrogen, fluoro, chloro, bromo, nitrile, ethyl, methyl, methoxy, ethoxy, acetyl and propanoyl.

6. The compound of claim 5 wherein $R^2$ is hydrogen.

7. The compound of claim 5 wherein $R^2$ is chloro or fluoro.

8. The compound of claim 5 wherein $R^2$ is nitrile.

9. The compound of claim 5 wherein $R^2$ is acetyl.

10. The compound of claim 3 wherein R is t-butyl, m is the integer 2 and n is the integer 0.

11. The compound of claim 10 wherein $R^2$ is hydrogen.

12. The compound of claim 10 wherein $R^2$ is chloro or fluoro.

13. The compound of claim 10 wherein $R^2$ is nitrile.

14. The compound of claim 10 wherein $R^2$ is acetyl.

15. The compound of claim 3 wherein R is isopropyl, m and n are the integer 1 and Y is the radical

16. The compound of claim 15 wherein $R^2$ is selected from the group hydrogen, fluoro, chloro, bromo, nitrile, ethyl, methyl, methoxy, ethoxy, acetyl and propanoyl and $R^5$ is hydrogen or methyl.

17. The compound of claim 16 wherein $R^2$ and $R^5$ are hydrogen.

18. The compound of claim 16 wherein $R^2$ is chloro or fluoro and $R^5$ is hydrogen.

19. The compound of claim 16 wherein $R^2$ is nitrile and $R^5$ is hydrogen.

20. The compound of claim 16 wherein $R^2$ is acetyl and $R^5$ is hydrogen.

21. A pharmaceutical composition for treating cardiovascular disorders in mammals by blocking the beta-adrenergic receptor sites, consisting essentially of a pharmaceutically acceptable carrier and an amount effective to block said beta-adrenergic receptor sites of an agent selected from the group of compounds of claim 1 and mixtures thereof.

22. A pharmaceutical composition for treating cardiovascular disorders in mammals by blocking the beta-adrenergic receptor sites, consisting essentially of a pharmaceutically acceptable carrier and an amount effective to block said beta-adrenergic receptor sites of an agent selected from the group of compounds of claim 2 and mixtures thereof.

23. A pharmaceutical composition for treating hypertension disorders in mammals consisting essentially of a pharmaceutically acceptable carrier and an amount effective to treat hypertension of an agent selected from the group of compounds of claim 1 and mixtures thereof.

24. A pharmaceutical composition for treating hypertension disorders in mammals consisting essentially of a pharmaceutically acceptable carrier and an amount effective to treat hypertension of an agent selected from the group of compounds of claim 2 and mixtures thereof.

25. The compound of claim 1 wherein said compound is a pharmaceutically acceptable salt, said salt selected from the group hydrochloride and maleate salt.

26. The compound of claim 1 wherein $R^1$ is

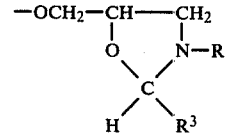

wherein R and $R^3$ are as previously defined and the pharmaceutically acceptable salts thereof.

27. The compound of claim 26 wherein R is selected from the group isopropyl and t-butyl.

28. The compound of claim 27 wherein R is isopropyl, m is the integer 2 and n is the integer 0.

29. The compound of claim 28 wherein $R^2$ is selected from the group hydrogen, fluoro, chloro, bromo, nitrile, ethyl, methyl, methoxy, ethoxy, acetyl and propanoyl.

30. The compound of claim 29 wherein $R^2$ and $R^3$ are hydrogen.

31. The compound of claim 29 wherein $R^2$ is hydrogen and $R^3$ is methyl.

32. The compound of claim 29 wherein $R^2$ is hydrogen and $R^3$ is phenyl.

33. The compound of claim 29 wherein $R^2$ is chloro or fluoro.

34. The compound of claim 29 wherein $R^2$ is nitrile.

35. The compound of claim 29 wherein $R^2$ is acetyl.

36. The compound of claim 27 wherein R is t-butyl.

37. The compound of claim 36 wherein $R^2$ is selected from the group hydrogen, fluoro, chloro, bromo, nitrile, ethyl, methyl, methoxy, ethoxy, acetyl and propanoyl.

38. The compound of claim 37 wherein $R^2$ and $R^3$ are hydrogen.

39. The compound of claim 37 wherein $R^2$ is hydrogen and $R^3$ is methyl.

40. The compound of claim 37 wherein $R^2$ is hydrogen and $R^3$ is phenyl.

41. The compound of claim 37 wherein $R^2$ is chloro or fluoro.

42. The compound of claim 37 wherein $R^2$ is nitrile.

43. The compound of claim 37 wherein $R^2$ is acetyl.

44. The compound of claim 27 wherein R is isopropyl, m and n are the integer 1 and Y is the radical $$>NR^5.$$

45. The compound of claim 44 wherein $R^2$ is selected from the group hydrogen, fluoro, chloro, bromo, nitrile, ethyl, methyl, methoxy, ethoxy, acetyl and propanoyl and $R^5$ is hydrogen or methyl.

46. The compound of claim 45 wherein $R^2$, $R^3$ and $R^5$ are hydrogen.

47. The compound of claim 45 wherein $R^2$ and $R^5$ are hydrogen and $R^3$ is methyl.

48. The compound of claim 45 wherein $R^2$ and $R^5$ are hydrogen and $R^3$ is phenyl.

49. The compound of claim 45 wherein $R^2$ is chloro or fluoro and $R^5$ is hydrogen.

50. The compound of claim 45 wherein $R^2$ is nitrile and $R^5$ is hydrogen.

51. The compound of claim 45 wherein $R^2$ is acetyl and $R^5$ is hydrogen.

52. The compound of claim 27 wherein R is t-butyl, m and n are the integer 1 and Y is the radical $$>NR^5.$$

53. The compound of claim 52 wherein $R^2$ is selected from the group hydrogen, fluoro, chloro, bromo, nitrile, ethyl, methyl, methoxy, ethoxy, acetyl and propanoyl and $R^5$ is hydrogen or methyl.

54. The compound of claim 53 wherein $R^2$, $R^3$ and $R^5$ are hydrogen.

55. The compound of claim 53 wherein $R^2$ and $R^5$ are hydrogen and $R^3$ is methyl.

56. The compound of claim 53 wherein $R^2$ and $R^5$ are hydrogen and $R^3$ is phenyl.

57. The compound of claim 53 wherein $R^2$ is chloro or fluoro and $R^5$ is hydrogen.

58. The compound of claim 53 wherein $R^2$ is nitrile and $R^5$ is hydrogen.

59. The compound of claim 53 wherein $R^2$ is acetyl and $R^5$ is hydrogen.

60. A pharmaceutical composition for treating cardiovascular disorders in mammals by blocking the beta-adrenergic receptor sites, consisting essentially of a pharmaceutically acceptable carrier and an amount effective to block said beta-adrenergic receptor sites of an agent selected from the group of compounds of claim 26 and mixtures thereof.

61. A pharmaceutical composition for treating hypertension disorders in mammals consisting essentially of a pharmaceutically acceptable carrier and an amount effective to treat hypertension of an agent selected from the group of compounds of claim 27 and mixtures thereof.

* * * * *